United States Patent [19]

Siren

[11] Patent Number: 5,846,957

[45] Date of Patent: Dec. 8, 1998

[54] USE OF AN ESTER OF INOSITOLTRISPHOSPHATE FOR THE PREPARING OF MEDICAMENTS

[75] Inventor: Matti Siren, Helsinki, Finland

[73] Assignee: Perstorp AB, Perstorp, Sweden

[21] Appl. No.: 648,175

[22] PCT Filed: Nov. 18, 1994

[86] PCT No.: PCT/SE94/01091

§ 371 Date: May 21, 1996

§ 102(e) Date: May 21, 1996

[87] PCT Pub. No.: WO95/14475

PCT Pub. Date: Jun. 1, 1995

[30] Foreign Application Priority Data

Nov. 22, 1993 [SE] Sweden .................................. 9303853

[51] Int. Cl.$^6$ .......................... A61K 31/66; A61K 31/215
[52] U.S. Cl. ............................................ 514/103; 514/530
[58] Field of Search ...................................... 514/103, 530

[56] References Cited

U.S. PATENT DOCUMENTS

| | | |
|---|---|---|
| 4,735,936 | 4/1988 | Siren . |
| 4,797,390 | 1/1989 | Siren . |
| 5,015,634 | 5/1991 | Siren . |
| 5,019,566 | 5/1991 | Siren . |
| 5,023,248 | 6/1991 | Siren . |
| 5,051,411 | 9/1991 | Siren . |
| 5,057,507 | 10/1991 | Siren . |
| 5,128,332 | 7/1992 | Siren et al. . |
| 5,135,923 | 8/1992 | Siren . |
| 5,330,979 | 7/1994 | Siren et al. . |
| 5,407,924 | 4/1995 | Siren . |
| 5,545,632 | 8/1996 | Siren . |

FOREIGN PATENT DOCUMENTS

| | | |
|---|---|---|
| 179439 | 4/1986 | European Pat. Off. . |
| 269105 | 6/1988 | European Pat. Off. . |
| WO 89/03220 | 4/1989 | WIPO . |
| WO 90/00057 | 1/1990 | WIPO . |

OTHER PUBLICATIONS

Harouse et al., *J. Of Virol.*, 63 (6):2527–2533 (Jun. 1989).
Zachar et al., *J. Of Virol.*, 65 (4):2102–2107 (Apr. 1991).
Bartlett, *New Engl. J. Of Med.*, 329 351–352 (Jul. 29, 1993).
Cooper et al., *New Engl. J. Of Med.*, 329 297–303 (Jul. 29, 1993).
Vince et al., *Biochem. Biophys. Res. Commun.* 156: 1046–1053 (1988).
Schultz et al., *Proc. Am. Assoc. Cancer Res.*, 33: 409, No. 2425 (1990).

Primary Examiner—Zohren Fay
Attorney, Agent, or Firm—Scully, Scott, Murphy & Presser

[57] ABSTRACT

The present invention relates to the use of an ester of inositoltrispbosphate for the preparing of a medicament effective against retroviral diseases.

24 Claims, No Drawings

USE OF AN ESTER OF INOSITOLTRISPHOSPHATE FOR THE PREPARING OF MEDICAMENTS

This application is a 371 of PCT/SE94/01091 filed on Nov. 181, 1994.

The present invention relates to the use of an ester of inositoltrisphosphate for the preparing of a medicament effective against retroviral diseases.

Acquired immunodeficiency syndrome (AIDS) is a serious immunodeficiency disease induced by human immunodeficiency virus (HIV), type 1 and type 2 (HIV-1 and HIV-2). HIV, which is the aetiological agent for AIDS is a nononcogenic, cytopathic retrovirus of the lentivirus subfamily. Retro-viruses have their genetic material in the form of RNA, ribonucleic acid, instead of DNA, deoxyribonucleic acid. In order to turn their RNA into DNA, retroviruses have a special enzyme called reverse transcriptase.

The HIV-virus, 100 nm in diameter is covered by an envelope, and contains a surface glycoprotein as well as an internal cylindrical core. The envelope is formed by phospholipids and glycoproteins and the core contains the genome and several enzymes.

HIV infects human cells primarily by binding to CD4 receptors on the surface of susceptible cells. This binding is mediated by the oligomeric envelope glycoprotein (gp) of HIV and the receptor on the target cell surface followed by the fusion between the viral envelope and the plasma membrane. The post-binding events which lead to membrane fusion are poorly understood but presumably include a conformational change in the envelope protein which exposes the hydrophopic amino terminus of a gp 41 envelope protein in the fusion reaction.

The binding of the HIV-1 envelope glycoprotein, gp 120, to the cellular receptor is the first step in HIV infection. However, there is also evidence for CD4 independent mechanism of infection. There are reports of HIV infection in a number of CD4-negative cells in vitro (Harouse, J. M. et al., J. Virol, 63, 2527, 1989, Zachar, V. B. et al. J. Virol, 65, 2102, 1991).

These data show that the expression of CD4 alone is not absolute obligatory and not sufficient to support HIV infection and implies that there are other molecules required for infection.

The patophysiological basis of the profound and irreversible immune depression following the infection is obscure.

AIDS was first recognized in 1981 in young, homosexual men from the U.S. with opportunistic infections, Kaposi's sarcoma, and primary CNS lymphoma. Although unusual cases of systemic malignant lymphoma were also recognised at that time, statistically significant increases were not apparent until 1985. Victims also suffered from other opportunistic infections, caused by microorganisms that are ubiquitous but ordinarily not able to cause disease. Indeed, the infections and cancers seen in AIDS patients were previously known only in people born with certain defects in their immune system.

Since the disease was first recognised the number of cases have risen swiftly. According to the World Health Organisation the increase of AIDS will result in up to 40 million people infected with HIV by the year 2000.

Recently the HIV infection has been classified into three distinct stages: the acute phase, lasting weeks, the chronic phase, lasting years, and the final phase of crisis (generally referred to as AIDS) lasting months to years.

AIDS is an unique disease. No other known infectious disease causes comparable harm by directly attacking the human immune system.

Once in the human body the virus attacks the cells that usually defend the body against infectious diseases. These cells include monocytes, macrophages and dendritic cells, so called antigen presenting cells (APC). Furthermore HIV can remain hidden in cells latent for months or years. A third difficulty is that HIV is extraordinary variable in its genetic make-up.

In 1985, zidovudine (AZT) was found to have in vitro activity against the human immunodeficiency virus, HIV. The in vitro and clinical activity of zidovudine is not disputed, but there is considerable debate when to initiate treatment (J. G. Bartlett,: New Engl. J. of Med., 329, 351, 1993; Cooper D. A. et al.: New Engl. J. of Med., 329, 297, 1993).

AZT can have serious side effects such as anaemia, and in people using the drug, HIV frequently mutates to produce strains that are unaffected by it.

Other nucleoside analogues are on trial but these will probably only be of limited usage as the mode of action including side effects ressemble those of zidovudine.

The function of AZT is to block the action of the enzyme reverse transcriptase of HIV which stops the virus from replicating in the cells.

Retroviruses vary at a notariously high rate resulting in rapid appearance of HIV-1 strains which are resistant against drugs and antibodies given to the patient. In addition several other stages in the HIV replicate cycle have been envisioned as targets for therapeutic intervention. One such target is the HIV protease which is essential for the assembly of fully infectious HIV particles.

In the past years an intensive search to find effective antiviral therapies has taken place. Active agents that have been discovered during the last years include carbovir (Vince, R. et al: Biochem. Biophys. Res. Commun. 156, 1046, 1988), and a class of oxathin benzoic acid esters and derivates (Schultz, R. J., et al.: Proc. Am. Assoc. Cancer Res. 33, 409, 1990).

While searching for a new drug which would prevent the spreading of HIV viruses, the following conditions should be fulfilled:

It should have no or few side effects, or at least these side effects should be minimal and tolerable.

It should have high therapeutic indices.

It should prevent the prolification of the HIV virus by preventing it from penetrating those cells in which the virus reproduces, or preventing it from reproducing inside these cells.

The half-life of the drug should be long enough to allow and administration once or twice daily.

The compound should be easily identified in the blood in order to establish individual dosage.

The drug should effect the target cell in the same form as it is administered and not only as a result of metabolic activity.

The drug should be teratologically safe.

According to the present invention it has surprisingly become possible to use an ester of inositoltrisphosphate for the preparing of a medicament effective against retroviral diseases.

In preferred embodiments of the invention the medicament is intended to be used for preventing, alleviating and combatting acquired immunodeficiency syndrome (AIDS) and AIDS-related diseases. The medicament can also be used against other conditions caused by retroviruses.

The medicament exerts significant inhibitory effects against retroviral infections without side-effects which is very beneficial for the patient.

Furthermore the medicament is also intended to be used against viral diseases caused by other enveloped viruses. For example the medicament is intended to be used against viral diseases caused by cytomegalovirus and different types of herpesvirus.

From the European Patent No 179439 a pharmaceutical composition comprising as a pharmaceutically active ingredient at least one isomer of inositoltrisphosphate is known. In said patent the effect of this pharmaceutical composition is shown for different areas, such as platelet aggregation.

The production of esters of inositoltrisphosphate and the isolation of the different isomers thereof are disclosed in the European Patent Application No. 0269105.

The therapeutic profile of esters of inositoltrisphosphates differs from the profile of inositoltrisphosphates in many important aspects. Chemical properties such as lipophilicity, solubility and $pK_A$-values are changed which affect the potency and selectivity of the compound.

Furthermore the susceptibility against enzymatic degradation is markedly lowered for esters of inositoltrisphosphates which result in a prolonged duration.

It is suitable that the medicament used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine. Other suitable administration forms are slow release and transdermal administration. A usual pharmaceutically acceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration. In other situations suspensions comprising the compound can be preferably used as administration form.

The medicament can also consist as such of esters of inositoltrisphosphate solely without any additive, excipient or carrier.

The medicament can consist of or comprise one or more specific isomers of esters of inositoltrisphosphate, each present in substantially pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

It is in most cases suitable that the ester of inositoltrisphosphate used for the preparing of the medicament according to the invention are present in salt form in order not to affect the mineral balance negatively. The salt should preferably consist of a sodium, potassium, calcium zinc or magnesium salt or a mixture of two or more of these salts.

For the above mentioned reasons it is also an advantage if the medicament contains a surplus or an extra addition of at least one pharmaceutically acceptable salt of calcium, zinc or magnesium with a mineral acid or organic acid. This is especially valuable for elderly persons who are often deficient in these minerals.

For administration to human patients appropriate dosages can routinely be determined by those skilled in this art by extension of the results obtained in animals at various dosages. The preferred dosage for humans falls within the range of 0.1 to 1000 mg, especially 0.1–200 mg of the compound/day/kg body weight.

In animal experiments, no toxic effects were seen after administration of very high doses of esters of inositoltrisphosphates, 300 mg/kg body weight by intravenous injection to mice.

The medicament usually contains 0.01–1.5 g, such as 0.05–1.3 g or preferably 0.1–1 g of the compound per unit dosage.

The composition used according to the present invention contains at least one, sometimes two or more of the following compounds, which correspond to esters of inositoltrisphosphates with the structural formula:

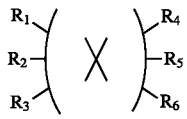

where $R_1$ $R_2$ and $R_3$ are vicinal and all are

where A is
(1) straight or branched chain alkyl containing 1 to 24 carbon atoms
(2) cycloalkyl containing 3 to 16 carbon atoms
(3) alkenyl containing 2 to 24 carbon atoms
(4) cycloalkenyl containing 5 to 16 carbon atoms
(5) aryl containing 6 to 24 carbon atoms
(6) aralkyl containing 7 to 48 carbon atoms
(7) alkaryl containing 7 to 48 carbon atoms
(8) aralkenyl containing 8 to 48 carbon atoms
(9) alkenylaryl containing 8 to 48 carbon atoms
(10) a heterocyclic ring containing at least one atom of oxygen, nitrogen or sulfur said meanings (1) to (10) being unsubstituted or substituted with hydroxy, oxo, alkoxy, aryloxy, halo, cyano, isocyano, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido
(11) carboxy
(12) esterified carboxy
(13) amino or
(14) substituted amino
where $R_4$, $R_5$ and R6 are vicinal and all are

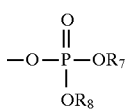

where $R_7$ and $R_8$ are the same or different and are
(1) hydrogen
(2) mono-, di- or trivalent cation
and where X is a radical of myo-inositol or a configuration isomer thereof.

The substituent A could be the same for all $R_1$, $R_2$ and $R_3$ or could have different structures following the above definition.

In another preferred embodiment of the invention $R_1$, $R_2$ and $R_3$ are vicinal and all are (1) 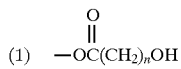

where n is an integer between 1 and 10; preferably n is between 2 and 4

(2) 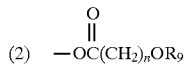

where n is an integer between 1 and 10 and where $R_9$ is a substituted or unsubstituted straight or branched alkyl, cycloalkyl, aryl or alkaryl; preferably n is between 2 and 4 and $R_9$ is a lower alkyl such as methyl, ethyl or propyl.

(3) 

where n and m is an integer between 1 and 10 and where Y is oxygen or sulphur; preferably n is 1 and m is between 2 and 4.

(4) 

where n and m is an integer between 1 and 10, where Y is oxygen or sulphur and where $R_9$ is a substituted or unsubstituted straight or branched alkyl, cycloalkyl, aryl or alkaryl; preferably n is 1, m is between 2 and 4 and $R_9$ is a lower alkyl such as methyl, ethyl or propyl.

(5) 

where n is an integer between 1 and 10 and where $R_9$ is a substituted or unsubstituted, straight or branched alkyl, cycloalkyl, aryl or aralkyl; preferably n is 1 or 2 and $R_9$ is a lower alkyl such as methyl, ethyl or propyl.

(6) 

where n is an integer between 1 and 10 and where $R_{10}$ is hydrogen or a substituted or unsubstituted, straight or branched alkyl, cycloalkyl, aryl or aralkyl; preferably n is 2 or 3 and $R_{10}$ is hydrogen or a lower alkyl such as methyl, ethyl or propyl.

(7) 

where n is an integer between 1 and 10 and where $R_9$ is a substituted or unsubstituted, straight or branched alkyl, cycloalkyl, aryl or aralkyl; preferably n is 1 and $R_9$ is a lower alkyl such as methyl, ethyl or propyl (8) 

where n is an integer between 1 and 10 and where $R_9$ is a substituted or unsubstituted, straight or branched alkyl, cycloalkyl, aryl or aralkyl, and where $R_{10}$ is hydrogen or substituted or unsubstituted, straight or branched alkyl, cycloalkyl, aryl or aralkyl; preferably n is 1, $R_9$ is lower alkyl such as methyl, ethyl or propyl and $R_{10}$ is hydrogen.

(9) 

where n is an integer between 1 and 10 and where $R_9$ is a substituted or unsubstituted, straight or branched alkyl, cycloalkyl, aryl or aralkyl and where $R_{10}$ is hydrogen or substituted or unsubstituted, straight or branched alkyl, cycloalkyl, aryl or aralkyl; preferably n is 1, $R_9$ is lower alkyl such as methyl, ethyl or propyl and $R_{10}$ is hydrogen.

(10) 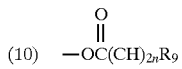

where n is an integer between 1 and 10 and where $R_9$ is a substituted or unsubstituted, straight or branched alkyl, cycloalkyl, aryl or aralkyl; preferably n is 1 and $R_9$ is a lower alkyl such as methyl, ethyl or propyl.

(11) 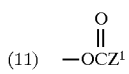

where $Z^1$ is substituted or unsubstituted cycloalkyl such as $CH(CH_2)_2$, $CH(CH_2)_3CH(CH_2)_4$, $CH(CH_2)_5$, $CH(CH_2)_6$ or $CH(CH_2)_2(CH)_2$.

(12) 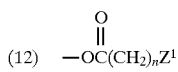

where $Z^1$ is substituted or unsubstituted cycloalkyl such as $CH(CH_2)_2$, $CH(CH_2)_3$, $CH(CH_2)_4$, $CH(CH_2)_5$, $CH(CH_2)_6$ or $CH(CH_2)_2(CH)_2$ and where n is an integer between 1 and 10; preferably n is 1.

(13) 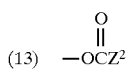

where $Z^2$ is substituted or unsubstituted phenyl, biphenyl, naphtyl, anthracenyl or phenantrenyl.

(14) 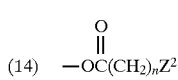

where $Z^2$ is substituted or unsubstituted phenyl, biphenyl, naphtyl, anthracenyl or phenantrenyl and where n is an integer between 1 and 10; preferably n is 1.

(15) 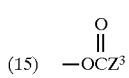

where $Z^3$ is substituted or unsubstituted heterocyclic compound such as

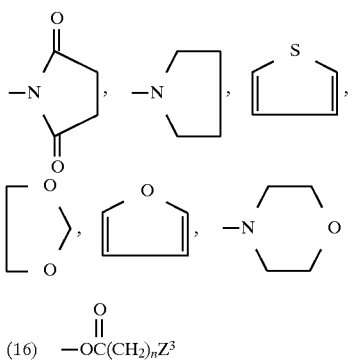

(16) $-OC(CH_2)_nZ^3$ where $Z^3$ is substituted or unsubstituted heterocyclic compound such as

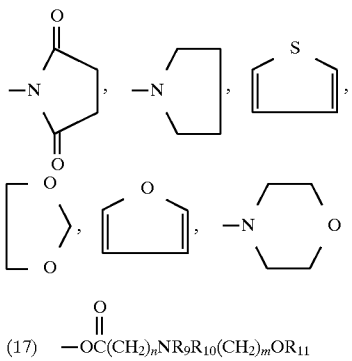

(17) $-OC(CH_2)_nNR_9R_{10}(CH_2)_mOR_{11}$ where n and m is an integer between 1 and 10, where $R_9$ is a substituted or unsubstituted, straight or branched alkyl, cycloalkyl, aryl, alkaryl and where $R_{10}$ and $R_{11}$ are hydrogen or substituted or unsubstituted straight or branched alkyl, cycloalkyl, aryl, alkaryl; preferably n is 1 or 2, m is 2 or 3, $R_9$ is lower alkyl and $R_{10}$ and $R_{11}$ are hydrogen.

(18) -O-acetyl, -O-propionyl, -O-butyryl, -O-isobutyryl, -O-(4-acetoxy)butyryl, -O-valeryl, -O-isovaleryl, -O-(4-propionyloxy)valeryl, -O-pivaloyl, -O-hexanoyl, -O-octanoyl, -O-decanoyl, -O-dodecanoyl, -O-tetradecanoyl, -O-hexadecanoyl or -O-octadecanoyl.

(19) -O-methylcarbamoyl, -O-ethylcarbamoyl, -O-propyl-carbamoyl, -O-butylcarbamoyl, -O-phenylcarbamoyl, -O-benzoylcarbamoyl, -O-(2-acetoxy) benzoylcarbamoyl, -O-(2-propionyloxy)benzoylcarbamoyl or chlorosulfonylcarbamoyl.

The above formula describes specific esters of inositoltrisphosphates where the inositol moiety is selected from the group of myoinositol, cisinositol, epiinositol, alloinositol, neoinositol, mucoinositol, chiroinositol and scylloinositol.

In one preferred embodiment of the invention the compound used for the preparing of a medicament effective against retroviral diseases has the structural formula

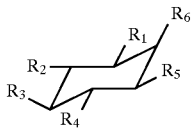

where $R_1$, $R_2$ and $R_3$ are vicinal and all are

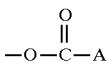

where A is
(1) straight or branched chain alkyl containing 1 to 24 carbon atoms
(2) cycloalkyl containing 3 to 16 carbon atoms
(3) alkenyl containing 2 to 24 carbon atoms
(4) cycloalkenyl containing 5 to 16 carbon atoms
(5) aryl containing 6 to 24 carbon atoms
(6) aralkyl containing 7 to 48 carbon atoms
(7) alkaryl containing 7 to 48 carbon atoms
(8) aralkenyl containing 8 to 48 carbon atoms
(9) alkenylaryl containing 8 to 48 carbon atoms
(10) a heterocyclic ring containing at least one atom of oxygen, nitrogen or sulfur said meaning (1) to (10) being unsubstituted or substituted with hydroxy, oxo, alkoxy, aryloxy, halo, cyano, isocyano, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or axido
(11) carboxy
(12) esterified carboxy
(13) amino or
(14) substituted amino
and where $R_4$, $R_5$ and $R_6$ all are

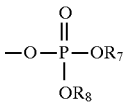

where $R_7$ and $R_8$ are the same or different and are
(1) hydrogen
(2) mono-, di- or trivalent cation.

The compounds contemplated in this embodiment of the invention are esters of myo-inositoltrisphosphates and preferred compounds are esters of D-myo-inositol-1,2,6-trisphosphates.

The invention will be further explained in the following examples where Example 1 shows the manufacturing of a solution of an ester of myo-inositoltrisphosphate for intravenous administration and Example 2–6 demonstrate the manufacture of different esters of myo-inositoltrisphosphate and Example 7 illustrates the inhibitory effect of an ester of myo-inositoltrisphosphate against HIV-induced infection. Example 8 demonstrates the ability of an ester of myo-inositoltrisphosphate to counteract infection induced by clinical isolates from HIV-patients and Example 9 shows the property of an ester of myo-inositol-trisphosphate to inhibit the spread of infection in a chronically infected culture.

EXAMPLE 1

Solution of the sodium salt of D-3,4,5-tri-O-hexanoyl-myoinositol-1,2,6-trisphosphate (PP 10-202) for injection 0.5 g of the sodium salt of PP 10-202 and 0.77 g sodium chloride were dissolved in 98.73 ml of water for injection to form a solution suitable for injection into a person or an animal.

EXAMPLE 2

1.92 mmol of the acid form of D-myo-inositol-1,2,6-trisphosphate ($IP_3$) was evaporated for the elimination of any residue of water and was then dissolved in 25 ml dimethylformamide (DMF). 1.24 g triethylamine was added followed by evaporation and an addition of 1.15 g 4-(dimethylamino)-pyridine. To this solution, 5.30 g 4-acetoxybutyric anhydride dissolved in 100 ml dimethylene chloride was added during 30 minutes. The reaction mixture was stirred for 3 hrs at room temperature and then evaporated to dryness. The residue was dissolved in 100 ml metanol and was extracted with 3×20 ml of heptane. The methanol-fraction was evaporated and the remaining product was analysed with NMR. Structural determination and NMR showed the compound to be D-3,4,5-tri-O-(4-acetoxybutyryl)-myo-inositol-1,2,6-trisphosphate.

EXAMPLE 3

In experiments similar to the procedure described in example 2 the following esters of D-myo-inositol-1,2,6-trisphosphate were synthesized in good yield;

D-3,4,5-tri-O-propionyl-myo-inositol-1,2,6-trisphosphate

D-3,4,5-tri-O-butyryl-myo-inositol-1,2,6-trisphosphate

D-3,4,5-tri-O-isobutyryl-myo-inositol-1,2,6-trisphosphate

D-3,4,5-tri-O-(4-hydroxy)pentanoyl-myo-inositol-1,2,6-trisphosphate

D-3,4,5-tri-O-dodecanoyl-myo-inositol-1,2,6-trisphosphate.

EXAMPLE 4

1.4 g of D-myo-inositol-1,2,6-tris(N-ethyldiisopropyl ammonium hydrogenphosphate) was dissolved in 15 ml methylene chloride. 1.59 g hexanoic anhydride, 1.4 ml N-ethyldiisopropylamine and 403 mg 4-(dimethylamino) pyridin was added and the reaction mixture was stirred for 16 hrs at 40° C. The solvent was removed by evaporation and to the residue was added 15 ml tetrahydrofuran and 20 ml water.

The resulting suspension was purified by ion exchange chromatography (Dowex 50W-X8) with water as eluent. The eluate was neutralized with sodium hydrogen carbonate and the water was removed. The residue was identified with NMR to be D-3,4,5-tri-O-hexanoyl,myo-inositol-trisphosphate.

EXAMPLE 5

5 g of the N-ethyldiisopropylamine salt of D-myo-inositol-1,2,6-trisphosphate was dissolved in 100 ml dimethylene methylene chloride. 1.44 g 4-(dimethylamino) pyridine and 5 ml etyldiisopropyl amine was added follow by dropwise addition of 5.75 ml phenylisocyanate during 60 minutes. The reaction mixture was stirred for 6 hours at room temperature and was then evaporated to dryness. The residue was dissolved in 30 ml tetrahydrofuran and 6 ml water followed by treatment with a cation exchange resin in H+-form. The product was eluted with 200 ml of water and was treated with sodium hydrogen carbonate to reach pH 5.8. After filtration the supernatant was evaporated to dryness and analysed with NMR. The compound was identified as D-3,4,5-tri-O-phenylcarbamoyl-myo-inositol-1,2,6-trisphosphate.

EXAMPLE 6

In experiments similar to the procedure described in example 5 the following carbamates of D-myo-inositol-1,2,6-trisphosphate were synthesized in good yield:

D-3,4,5-tri-O-(2-acetoxy)benzoyl carbamoyl-1,2,6-trisphosphate

D-3,4,5-tri-O-butylcarbamoyl-1,2,6-trisphosphate

D-3,4,5-tri-o-methylcarbamoyl-1,2,6-trisphosphate

EXAMPLE 7

Inhibitory effect of the sodium salt of D-3,4,5-tri-O-hexanoyl-myo-inositol-1,2,6-trisphosphate (PP 10-202) on HIV-induced infection.

Three preparations of H 9 cells were chronically infected by HIV-3B (type code of HIV-virus) and mixed with uninfected C 8166 cells. This mixture formed a number of syncytia-cells with more than five nucleus and ballooning cytoplasm.

One of the preparations were used as a control, while the second preparation was incubated with a soluble recombinant CD4 (10 µg/ml) which is known to inhibit syncytia-formation. The third preparation was incubated with PP 10-202 (1000 µg/ml).

All preparations were investigated after 24 hours with a microscope in order to determine the progress of the infection.

In the control preparation a large increase of syncytia-cells was determined which showed that the progress of infection was high and severe. The preparation with soluble CD4 showed a marked inhibition of syncytia-formation. In the preparation with PP 10-202 the formation of syncytia-cells was completely blocked after 24 hours without any morphologically apparent cytotoxicity.

The usage of PP 10-202 showed a strong inhibitory effect against HIV-induced infection.

EXAMPLE 8

Viral isolates from HIV-infected patients were used in order to induce an infection by adding peripheral blood mononuclear cells (PBMC) to a medium containing different concentrations of the sodium salt of D-3,4,5-tri-O-hexanoyl-myo-inositol-1,2,6-trisphosphate (PP10-202). 25 $CCID_{50}$ (50% cell culture infections dose) of PBMCs from HIV-infected patients were incubated with four different concentrations of PP10-202; 0.0625 mg/ml, 0.125 mg/ml, 0.250 mg/ml and 0.500 mg/ml. Another preparation, without any PP10-202 served as a control. The growth medium consisted of 10 % fetal calf serum, 2 µM glytamine, 100 IU/ml penicillin, 100 IU/ml streptomycin and 20 µg/ml gentamicin. The concentration of cells were $2\times10^5$ per ml. All preparations were incubated for 1 hour at 37° C.

PBMCs from healthy donors were then added to the preparation. Before addition, these cells were stimulated for three days with phytohemagglutinin (PHA). $0.5\times10^6$ PHA-stimulated PBMCs were added to each preparation, followed by incubation for 3 hours at 37° C. After extensive washing the cells were resuspended in growth medium supplemented with 10 IU/ml of interleukin-2 and seeded in quadruplicates of 100.000 cells in a 96-well microtite plate before further cultivation for 7 days. The HIV-antigen production was assayed at the seventh day using an ELISA-technique. The obtained values were normalized and are summarized in the following table:

| Concentration of PP10-202 mg/ml | HIV-infection (%) |
|---|---|
| 0 | 100 |
| 0.0625 | 75 |
| 0.125 | 41 |
| 0.250 | 33 |
| 0.500 | 20 |

In this example, where the HIV-infection is induced by clinical isolates from HIV-infected patients, PP10-202 shows a strong effect to counteract the infection.

EXAMPLE 9

Newly separated peripheral blood mononuclear cells (PBMCs) were stimulated for three days with phytohemagglutinin (PHA-P) and then infected with a large inoculum of a low passage clinical isolate of HIV. The infected cells were cultured for four days and then mixed with uninfected PHA-P-stimulated PBMCs at a ratio of 1:11. After pelletation half of the cells were resuspended in unsupplemented medium and half of the cells in a medium supplemented with the sodium salt of D-3,4,5-tri-O-hexanoyl-myo-inositol-1,2,6-trisphosphate (PP10-202) at a concentration of 0.5 mg/ml. The resuspended cells were plated in quadruplicates in a 24 well microtites plate with $0.5 \times 10^6$ cells in each well and cultured. Half the medium was harvested twice a week and new medium with or without PP10-202 was added. The amount of HIV-antigen present in the supernatant was evaluated using an ELISA-technique after 4, 7 and 10 days of culture. A high amount of antigen corresponds to an increased infection. The obtained data are shown in the following table:

| Amount of HIV-antigen (AU/ml) | Day 4 | Day 7 | Day 10 |
|---|---|---|---|
| PP10-202, 0.5 mg/ml | 5.4 | 7.1 | 5.6 |
| Control | 180 | 606 | 264 |

The results show that the addition of PP10-202 to the medium very markedly decreases the already infected culture. The example is very predictive to a clinical situation where the administration of an active compound normally starts after the initiation of the disease.

I claim:

1. A method of treating a retroviral disease in a mammal comprising administering to a mammal in need thereof a treatment effective amount of an ester of inositol triphosphate.

2. A method according to claim 1 wherein the disease is acquired immuno deficiency syndrome (AIDS) or an AIDS-related disease.

3. The method of claim 1 or 2 wherein said ester of inositoltrisphosphate is in a salt form.

4. The method according to claim 3 wherein said ester of inositoltrisphosphate is present as a salt of sodium, potassium, calcium or zinc.

5. The method of claim 1 or 2 wherein said ester of inositoltrisphosphate is an ester of myo-inositoltrisphosphate.

6. The method of claim 1 or 2 wherein said ester of inositoltrisphosphate is an ester of D-myo-inositol-1,2,6-trisphosphate.

7. The method in accordance with claim 1 wherein said ester of inositoltrisphosphate is administered in a unit dosage form.

8. The method in accordance with claim 7 wherein said unit dosage is provided in the form of a tablet, granule, capsule, solution or suspension.

9. The method according to claim 1 wherein the mammal is a human.

10. The method according to claim 1 wherein the ester of inositoltrisphosphate has the formula

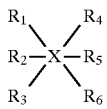

where $R_1$, $R_2$ and $R_3$ are vicinal and all are

where each A may be the same or different and is (a) straight or branched chain unsubstituted or substituted alkyl containing 1 to 24 carbon atoms;

(b) unsubstituted or substituted cycloalkyl containing 3 to 16 carbon atoms;

(c) unsubstituted or substituted alkenyl containing 2: to 24 carbon atoms;

(d) unsubstituted or substituted cycloalkenyl containing 5 to 16 carbon atoms;

(e) unsubstituted or substituted aryl containing 6 to 24 carbon atoms;

(f) unsubstituted or substituted aralkyl containing 7 to 48 carbon atoms;

(g) unsubstituted or substituted alkaryl containing 7 to 48 carbon atoms;

(h) unsubstituted or substituted aralkenyl containing 8 to 48 carbon atoms;

(i) unsubstituted or substituted alkenylaryl containing 8 to 48 carbon atoms;

(j) a heterocyclic ring, said heterocyclic being

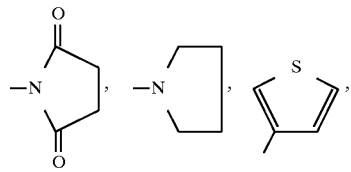

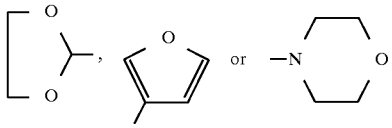

said A being unsubstituted or substituted with hydroxy, oxo, alkoxy, aryloxy, halo, cyano, isocyano, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido;

(k) carboxy;

(l) esterified carboxy;

(m) amino; or (n) substituted amino where $R_4$, $R_5$ and $R_6$ are vicinal and all are

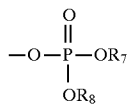

where $R_7$ and $R_8$ are the same or different and are (i) hydrogen or;

(ii) mono-, di- or trivalent cation;

and where X is a radical of myo-inositol or a configuration isomer thereof.

11. The method according to claim 10 wherein $R_1$, $R_2$ and $R_3$ are the same.

12. The method according to claim 10 wherein $R_1$, $R_2$ and $R_3$ are independently

 (a)

where n is an integer between 1 and 10,

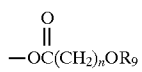 (b)

where n is an integer between 1 and 10 and where $R_9$ is a substituted or unsubstituted straight or branched alkyl, cycloalkyl, aryl or alkaryl;

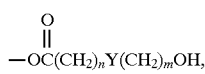 (c)

where n and m are independently an integer between 1 and 10 and where Y is oxygen or sulphur;

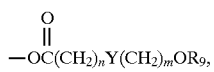 (d)

where n and m are independently an integer between 1 and 10 and where Y is oxygen or sulphur and where $R_9$ is a substituted or unsubstituted straight or branched alkyl, cycloalkyl, aryl or alkaryl;

 (e)

where n is an integer between 1 and 10 and where $R_9$ is a substituted or unsubstituted, straight or branched alkyl, cycloalkyl, aryl or aralkyl;

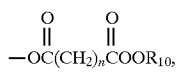 (f)

where n is an integer between 1 and 10 and where $R_{10}$ is hydrogen or a substituted or unsubstituted, straight or branched alkyl, cycloalkyl, aryl or aralkyl;

 (g)

where n is an integer between 1 and 10 and where $R_9$ is a substituted or unsubstituted, straight or branched alkyl, cycloalkyl, aryl or aralkyl;

 (h)

where n is an integer between 1 and 10 and where $R_9$ is a substituted or unsubstituted, straight or branched alkyl, cycloalkyl, aryl or aralkyl, and where $R_{10}$ is hydrogen or substituted or unsubstituted, straight or branched alkyl, cycloalkyl, aryl or aralkyl;

 (i)

where n is an integer between 1 and 10 and where $R_9$ is a substituted or unsubstituted, straight or branched alkyl, cycloalkyl, aryl or aralkyl and where $R_{10}$ is hydrogen or substituted or unsubstituted, straight or branched alkyl, cycloalkyl, aryl or aralkyl;

 (j)

where n is an integer between 1 and 10 and where $R_9$ is a substituted or unsubstituted, straight or branched alkyl, cycloalkyl, aryl or aralkyl;

 (k)

where $Z^1$ is substituted or unsubstituted cycloalkyl;

 (l)

where $Z^1$ is substituted or unsubstituted cycloalkyl and where n is an integer between 1 and 10;

 (m)

where $Z^2$ is substituted or unsubstituted phenyl, biphenyl, naphthyl, anthracenyl or phenantrenyl;

 (n)

where $Z^2$ is substituted or unsubstituted phenyl, biphenyl, naphthyl, anthracenyl or phenanthrenyl, and where n is an integer between 1 and 10;

 (o)

where $Z^3$ is substituted or unsubstituted heterocyclic selected from the group consisting of

 (p)

-continued

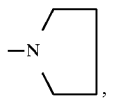

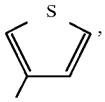

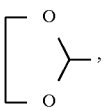

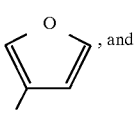

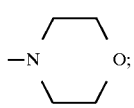

where $Z^3$ is substituted or unsubstituted heterocyclic compound selected from the group consisting of

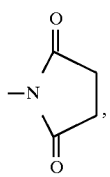 (q)

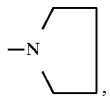

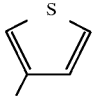

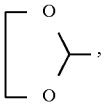

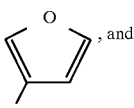

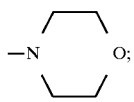

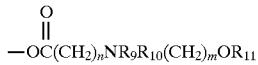

where n and m are independently an integer between 1 and 10, where $R_9$ is a substituted or unsubstituted, straight or branched alkyl, cycloalkyl, aryl, alkaryl and where $R_{10}$ and $R_{11}$ are independently hydrogen or substituted or unsubstituted straight, or branched alkyl, cycloalkyl, aryl, alkaryl;

(r) O-acetyl, O-propionyl, O-butyryl, O-isobutyryl, O-(4-acetoxy)butyryl, O-valeryl, O-isovaleryl, O-(4-propionyloxy)valeryl, O-pivaloyl, O-hexanoyl, O-octanoyl, O-decanoyl, O-dodecanoyl, O-tetradecanoyl, O-hexadecanoyl or O-octadecanoyl; or (s) O-methylcarbomoyl, O-ethylcarbamoyl, O-propylcarbamoyl, O-butylcarbamoyl, O-phenylcarbamoyl, O-benzoylcarbamoyl, O-(2-acetoxy) benzoylcarbamoyl, O-(2-propionyloxy) benzoylcarbamoyl or chlorosulfonylcarbamoyl.

13. The method according to claim 10 wherein X is myoinositol, cisinositol, epiinositol, alloinositol, neoinositol, mucoinositol, chiroinositol, or scylloinositol.

14. The method according to claim 12 wherein $R_1$, $R_2$ and $R_3$ are the same.

15. The method according to claim 12 wherein $R_1$, $R_2$ and $R_3$ are the same and are

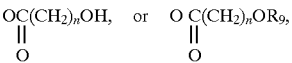

and n is 2–4 and $R_9$ is methyl, ethyl or propyl.

16. The method according to claim 12 wherein $R_1$, $R_2$ and $R_3$ are

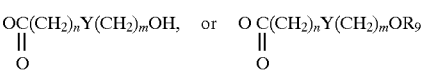

wherein n is 1, m is 2–4, and $R_9$ is methyl, ethyl or propyl.

17. The method according to claim 12 wherein $R_1$, $R_2$ and $R_3$ are

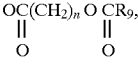

wherein $R_9$ is methyl, ethyl or propyl and n is 1 or 2.

18. The method according to claim 12 wherein $R_1$, $R_2$ and $R_3$ are

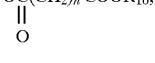

wherein n is 2 or 3 and $R_{10}$ is H, methyl, ethyl or propyl.

19. The method according to claim 12 wherein $R_1$, $R_2$ and $R_3$ are the same and are

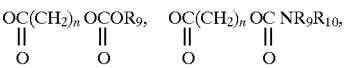

wherein n is 1, $R_9$ is methyl, ethyl or propyl and $R_{10}$ is hydrogen.

20. The method according to claim 12, wherein $R_1$, $R_2$ and $R_3$ are the same and are

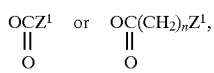

wherein Z is $CH(CH)_2$, $CH(CH_2)_3$, $CH(CH_2)_4$, $CH(CH_2)_5$, $CH(CH_2)_6$, or $CH(CH_2)_2CH_2$, and n is 1.

21. The method according to claim 12, wherein $R_1$, $R_2$ and $R_3$ are the same and are

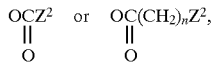

wherein $Z^2$ is substituted or unsubstituted phenyl, biphenyl, naphthyl, anthracenyl or phenantrenyl;, and n is 1.

22. The method according to claim 12 wherein $R_1$, $R_2$ and $R_3$ are

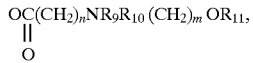

wherein n is 1 or 2, m is 2 or 3, $R_9$ is methyl, ethyl or propyl and $R_{10}$ and $R_{11}$ are hydrogen.

23. The method according to claim 10 wherein the inositoltrisphosphate is

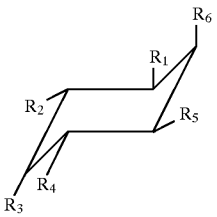

24. The method according to claim 1 wherein said ester of inositoltrisphosphate has three esterified inositol hydroxy groups.

* * * * *

UNITED STATES PATENT AND TRADEMARK OFFICE
CERTIFICATE OF CORRECTION

PATENT NO. : 5,846,957
DATED : December 8, 1998
INVENTOR(S) : Lars Persson, et al.

It is certified that error appears in the above-identified patent and that said Letters Patent is hereby corrected as shown below:

On The Title Page, [57] ABSTRACT: "inositoltrispbosphate" should read

--inositoltrisphosphate--

Column 1, Line 6: "NOV. 181, 1994" should read --NOV. 18, 1994--

Column 11, Lines 49 and 50, Claim 1: "inositol triphosphate" should read

--inositoltrisphosphate--

Column 12, Line 26, Claim 10: "2:to" should read --2 to--

Column 14, Line 20, Claim 12(i): "$-O\overset{O}{\overset{\|}{C}}(CH)_{2n}R_9$" should read --$O\overset{O}{\overset{\|}{C}}(CH_2)_nR_9-$--

Column 14, Line 60, Claim 12: "(p)" Should be in column 15, Line 25.

UNITED STATES PATENT AND TRADEMARK OFFICE
CERTIFICATE OF CORRECTION

PATENT NO. : 5,846,957
DATED : December 8, 1998
INVENTOR(S) : Lars Persson, et al.

It is certified that error appears in the above-identified patent and that said Letters Patent is hereby corrected as shown below:

Column 15, Line 31, Claim 12: "(q)" should be on line 62.

Column 16, Line 10, Claim 12: "O-methylcarbomoyl" should read --O-methylcarbamoyl--

Column 16, Line 60, Claim 19: "$O\overset{O}{\underset{\|}{C}}(CH_2)_{2n} R_9$" should read --$O\overset{O}{\underset{\|}{C}}(CH_2)_n R_9$--

Signed and Sealed this

Twenty-ninth Day of May, 2001

Attest:

NICHOLAS P. GODICI

Attesting Officer          Acting Director of the United States Patent and Trademark Office